US00PP27599P3

(12) United States Plant Patent
Lee

(10) Patent No.: US PP27,599 P3
(45) Date of Patent: Jan. 24, 2017

(54) ***GARDENIA* PLANT NAMED 'LEETHREE'**

(50) Latin Name: *Gardenia hybrida*
Varietal Denomination: LEETHREE

(71) Applicant: Robert Edward Lee, Independence, LA (US)

(72) Inventor: Robert Edward Lee, Independence, LA (US)

(73) Assignee: PDSI, Loxley, AL (US)

( * ) Notice: Subject to any disclaimer, the term of this patent is extended or adjusted under 35 U.S.C. 154(b) by 169 days.

(21) Appl. No.: 14/121,180

(22) Filed: Aug. 11, 2014

(65) Prior Publication Data

US 2016/0044849 P1 Feb. 11, 2016

(51) Int. Cl.
*A01H 5/02* (2006.01)

(52) U.S. Cl.
USPC ..... Plt./255

(58) Field of Classification Search
USPC ..... Plt./255
See application file for complete search history.

*Primary Examiner* — Keith Robinson
(74) *Attorney, Agent, or Firm* — Cassandra Bright

(57) ABSTRACT

A new and distinct *Gardenia* cultivar named 'LEETHREE' is disclosed, characterized by distinctive small, perfectly radial, very fragrant, white flowers Plants are small and compact, dense and suitable for Southern climates. The new cultivar is a *Gardenia*, suitable for ornamental garden purposes.

2 Drawing Sheets

Latin name of the genus and species: *Gardenia hybrida.*
Variety denomination: 'LEETHREE'.

BACKGROUND OF THE INVENTION

The new cultivar is a product of a planned breeding program by the inventor. This new variety, hereinafter referred to as 'LEETHREE', was found as an openly pollinated seedling in a group of *Gardenia jasminoides* 'Daisy' (unpatented) seedling plants being grown in Independence, La. The inventor, Robert Edward Lee, discovered the seedling in Independence, La., at a research nursery during October of 2000.

After identifying the new variety as a potentially interesting selection, the inventor first organized propagation of 'LEETHREE' by vegetative cuttings during 2004 at the same commercial nursery in Independence, La. The inventor continued confidential, controlled testing and propagation, assessing stability of the unique characteristics of this variety. Multiple generations have been reproduced and have shown that the unique features of this cultivar are stable and reproduced true to type.

SUMMARY OF THE INVENTION

The cultivar 'LEETHREE' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'LEETHREE' These characteristics in combination distinguish 'LEETHREE' as a new and distinct *Gardenia* cultivar:

1. Unique, perfectly radial, single flower form.
2. Tolerance for heat and disease
3. Adaptability to production and use in Southern climates.

4. Excellent fragrance.
5. Extremely compact growth
6. Deep green, shiny foliage
7. Good specimen plant
8. Good container plant

COMPARISON TO PARENT VARIETY

'LEETHREE' is similar in most horticultural characteristics to the seed parent variety *Gardenia* 'Daisy' unpatented. Plants of the new cultivar 'LEETHREE' however, produce flowers that smaller and stronger, than the seed parent variety. Additionally, plant habit is overall more compact in the new variety, than the seed parent.

The pollen parent is unknown.

COMMERCIAL COMPARISON

'LEETHREE' can be compared to the commercial variety *Gardenia hybrida* 'LEETWO', U.S. Plant patent application Ser. No. 14/121,171. Plants of the new cultivar 'LEETHREE' are similar to plants of 'LEETWO' in most horticultural characteristics, however, plants of the new cultivar 'LEETHREE' produce flowers that are smaller, and overall plant size of 'LEETHREE' is smaller.

BRIEF DESCRIPTION OF THE PHOTOGRAPHS

Figure 1:
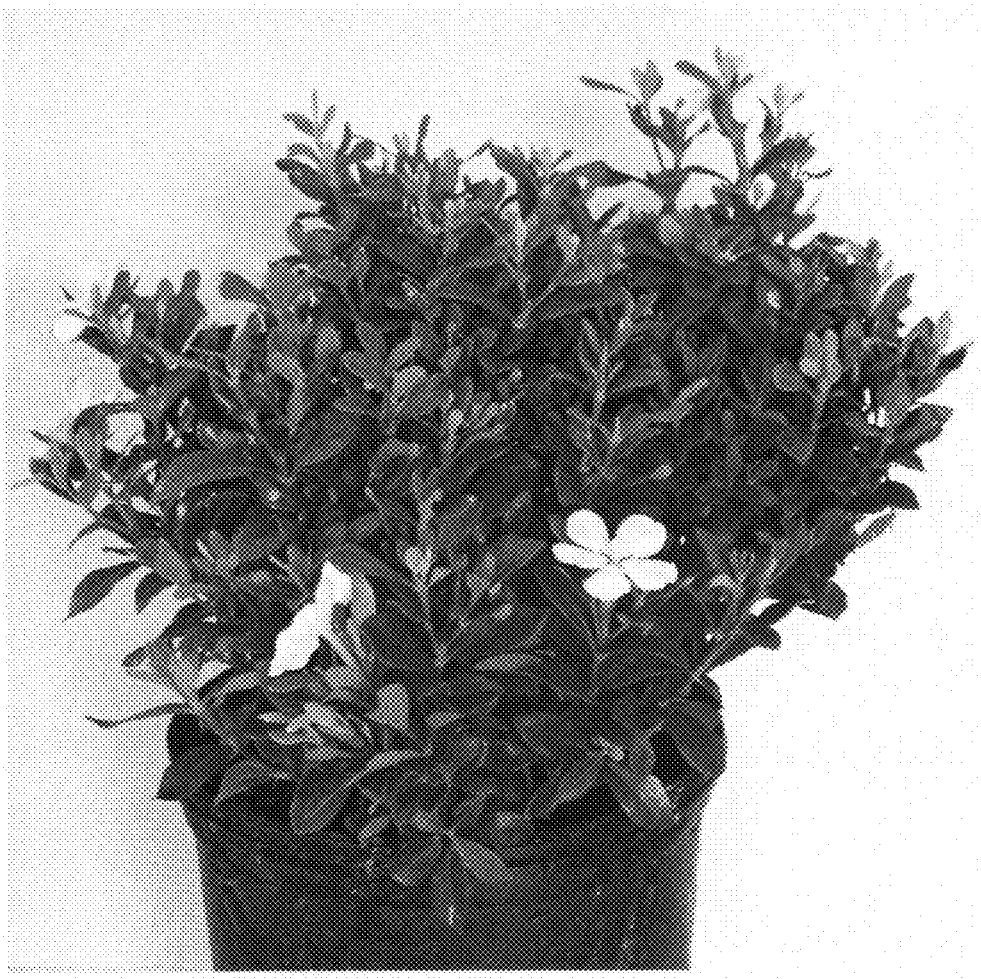

The accompanying photograph in FIG. 1 illustrates in full color a plant of 'LEETHREE' grown outdoors in Alabama.

Figure 2:
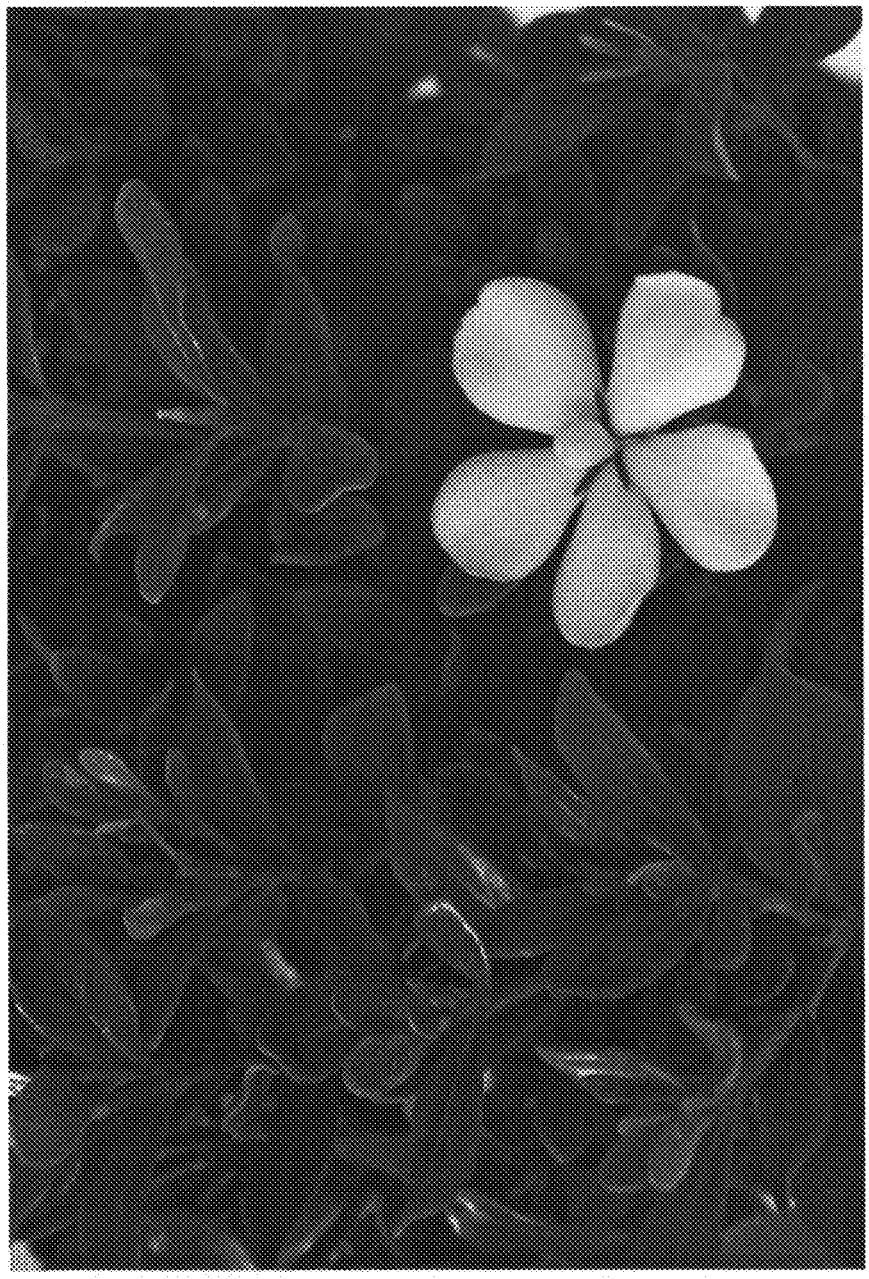

FIG. 2 shows a close up of a typical flower of the new variety. The plant is approximately 2 years old, and is shown in a three gallon container. The photographs were taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'LEETHREE' plants grown outdoors in Loxley, Ala. Plants are approximately 2 years old, in a 3 gallon nursery container. Measurements and numerical values represent averages of typical plant types.

Botanical classification: *Gardenia hybrida* 'LEETHREE'.

PROPAGATION

Typically by semi-hardwood cuttings in Spring and Summer.

Root description: Woody to semi-wood. Colored near RHS Brown 200D.

Time to initiate roots: About 4 to 6 weeks in the Summer.

Time to produce a rooted young plant: Approximately 12 weeks in the Summer.

PLANT

Growth habit: Globular shrub.

Height: Approximately 38 cm to top of foliar and flowering plane.

Plant spread: Approximately 40 cm.

Branching characteristics: Well branched, approximately 4 to 6 lateral branches emerge from a pinch. Some smaller lateral branches occurring with pinch. Branches occur at approximately 15° to 35° angles.

Primary branches:

- *Length of primary branches.*—Average 10 cm, then pinched and new branches emerge.
- *Diameter of primary branches.*—Approximately 1.2 cm.
- *Primary branch strength.*—Very strong, flexible, difficult to break.
- *Primary branch color.*—Mature branches are colored, near Red-Purple 183A with striation near Greyed-Green 198A. Young branches near Yellow-Green 147A.
- *Primary branch texture.*—Mature branches rough. Young growth slightly rough and slightly canescent.

Lateral branches:

- *Color.*—Near RHS Yellow-Green 147A.
- *Length.*—Average range 10 to 28 cm.
- *Diameter.*—Approximately 0.4 cm.
- *Aspect.*—Straight, attached at acute angles.
- *Texture.*—Slightly canescent.
- *Strength.*—Strong, flexible.
- *Internode.*—Average range 1.4 cm to 3.7 cm.

Age of plant described: Approximately 2 years.

FOLIAGE

Leaf:

- *Type.*—Simple.
- *Arrangement.*—Opposite.
- *Average length.*—Approximately 4.2 cm.
- *Average width.*—Approximately 1.7 cm.
- *Shape of blade.*—Elliptic.
- *Apex.*—Acute.
- *Base.*—Broad attenuate.
- *Attachment.*—Sessile.
- *Margin.*—Entire.
- *Internode.*—Average 2.8 cm.
- *Texture of top surface.*—Glabrous.
- *Texture of bottom surface.*—Glabrous.
- *Appearance of top surface.*—Glossy.
- *Appearance of bottom surface.*—Matte.
- *Color.*—Young foliage upper side: Near RHS Yellow-Green 144A. Young foliage under side: Near RHS Yellow-Green 146D. Mature foliage upper side: Near RHS Green 139A. Mature foliage under side: Near RHS Green 137D.
- *Venation.*—Type: Pinnate. Venation color upper side: Near RHS Yellow-Green 146D. Venation color under side: Near RHS Yellow-Green 146D.

FLOWER

Bloom period: Plants flower in the Spring, then begin intermittent flowering cycles in late Spring/Summer through Fall in Southern California.

Inflorescence:

- *Arrangement.*—Single rotate flowers arise from upper leaf axils.

Peduncle:

- *Length.*—Average 0.9 cm.
- *Diameter.*—0.3 cm.
- *Color.*—Near RHS Green 143A.
- *Texture.*—Pubescent.
- *Aspect.*—Straight. Angle of attachment, approximately 15° angle from stem.
- *Strength.*—Moderately strong and flexible.

Flowers:

- *Arrangement.*—Single rotate flowers arise from upper leaf axils. Height: Average 5.5 cm. Diameter: Average 4.0 cm. Facing direction: Outwardly and upwardly facing. Persistent or self-cleaning: Flowers persist until completely dried up, then fall off. Fragrance: Very strong, sweet fragrance.
- *Tube.*—Tube length: Approximately 3.5 cm. Tube width a widest point: Approximately 0.6 cm. Tube width and narrowest point: Approximately 0.3 cm.
- *Petals.*—Unfused petal segments: Length: Approximately 2.3 cm. Width: Approximately 1.6 cm. Apex: Rounded. Base: Fused at base into tube. Shape of petal: Unfused portion, spatulate. Petal margin: Entire. Petal Arrangement: Rotate, not overlapping, fused approximately ⅓ from base. Petal Number: 6. Petal Texture: Smooth, upper and lower surfaces.
- *Color.*—Upper surface at first opening: Near RHS White 155C. Under surface at first opening: Near RHS White 155C. Inner surface at maturity: Near RHS White 155C. Outer surface at maturity: Near RHS White 155C. Upper surface at fading: Near RHS White 155C. Under surface at fading: Near RHS White 155C.

Bud:

- *Shape.*—Elliptic.
- *Length.*—2.4 cm.
- *Diameter.*—1.6 cm.
- *Color.*—Near RHS White 155C and Green-White 157A.

Calyx/sepals:

- *Quantity per flower.*—5 sepals.
- *Arrangement.*—Rotate.
- *Shape.*—Narrow deltate, base fused.
- *Length.*—Average 1.1 cm.
- *Width.*—0.2 cm.
- *Apex.*—Acute.
- *Base.*—Fused.

*Margin*.—Entire.

*Texture*.—Very slightly pubescent all surfaces. Color: Inner Surface: Near RHS Green 143B. Outer Surface: Near RHS Green 138A.

REPRODUCTIVE ORGANS

Stamens:

*Number*.—6, except anthers, androeceium fused to floral tube.

*Length*.—0.7 cm, anthers only.

*Width*.—0.1 cm.

*Anthers*.—Anthers reflexed back, and attached to petals. Length: Approximately 0.7 cm. Width: Approximately 0.1 cm. Color: Near RHS Greyed-Orange 175A. Pollen: Scant, colored near Greyed-Orange 164C. Shape: Linear to crescent.

Pistil:

*Number*.—1.

*Length*.—4.5 cm.

*Style*.—Length: 3.5 cm. Color: Near RHS Green-White 157A.

*Stigma*.—4 lobed globular, colored near 158A.

*Ovary*.—Approximately 0.3 cm in diameter, 0.4 long. Colored near Green 143A.

OTHER CHARACTERISTICS

Disease and pest resistance: Observed to be less susceptible to normal diseases and pests of *Gardenia hybrida*. Typical diseases of *Gardenia* include *Erysiphe polygoni*, and *Phomopsis gardenia*. Pests include the nematode *Meloidogyne* spp., white fly *Dialeurodes citri* and various scales, including *Ceroplastes japonicas, Icerya purchase, Fiorinia theae, Hemiberlesia rapax* and *Aspidiotus nerii*.

Temperature Tolerance: USDA Zone 8.

Fruit/seed production: Not observed to date.

What is claimed is:

1. new and distinct cultivar of *Gardenia* plant named 'LEETHREE' as herein illustrated and described.

* * * * *